US012697492B2

(12) United States Patent　　　(10) Patent No.: US 12,697,492 B2
Casavant et al.　　　　　　　　　(45) Date of Patent: *Aug. 4, 2026

(54) ADJUSTABLE SENSING IN A HIS-BUNDLE PACEMAKER

(71) Applicant: Cardiac Pacemakers, Inc., St. Paul, MN (US)

(72) Inventors: David Arthur Casavant, Reading, MA (US); David L. Perschbacher, Blaine, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 280 days.

This patent is subject to a terminal disclaimer.

(21) Appl. No.: 18/421,642

(22) Filed: Jan. 24, 2024

(65) Prior Publication Data

US 2024/0157153 A1　　May 16, 2024

Related U.S. Application Data

(63) Continuation of application No. 17/940,886, filed on Sep. 8, 2022, now Pat. No. 11,918,814, which is a
(Continued)

(51) Int. Cl.
*A61N 1/00* (2006.01)
*A61B 5/349* (2021.01)
(Continued)

(52) U.S. Cl.
CPC .............. *A61N 1/365* (2013.01); *A61B 5/349* (2021.01); *A61B 5/364* (2021.01)

(58) Field of Classification Search
None
See application file for complete search history.

(56) References Cited

U.S. PATENT DOCUMENTS 4,548,203 A　10/1985　Tacker, Jr. et al.
4,559,946 A　12/1985　Mower
(Continued)

FOREIGN PATENT DOCUMENTS

CN　　112543662 A　　3/2021
EP　　0467652　　1/1992
(Continued)

OTHER PUBLICATIONS

"U.S. Appl. No. 16/459,092, Examiner Interview Summary mailed May 10, 2021", 2 pgs.
(Continued)

*Primary Examiner* — William J Levicky
*Assistant Examiner* — Anant A Gupta
(74) *Attorney, Agent, or Firm* — Nelson Mullins Riley & Scarborough LLP

(57) ABSTRACT

Systems and methods for pacing cardiac conductive tissue are described. An embodiment of a medical system includes an electrostimulation circuit to generate His-bundle pacing (HBP) pulses to stimulate a His bundle, and a cardiac event detector to detect a His-bundle activity within a time window following an atrial activity. The cardiac event detector may use a cross-chamber blanking, or an adjustable His-bundle sensing threshold, to avoid or reduce over-sensing of far-field atrial activity and inappropriate inhibition of HBP therapy. The electrostimulation circuit may deliver HBP in the presence of the His-bundle activity. The system may further recognize the detected His-bundle activity as either a FFPW or a valid inhibitory event, and deliver or withhold HBP therapy based on the recognition of the His-bundle activity.

20 Claims, 5 Drawing Sheets

Related U.S. Application Data continuation of application No. 16/459,092, filed on Jul. 1, 2019, now Pat. No. 11,458,319.

(60) Provisional application No. 62/694,825, filed on Jul. 6, 2018.

(51) Int. Cl.
　　*A61B 5/364*　　　(2021.01)
　　*A61N 1/365*　　　(2006.01)

(56) References Cited

U.S. PATENT DOCUMENTS

| | | | |
|---|---|---|---|
| 4,637,397 | A | 1/1987 | Jones et al. |
| 4,641,656 | A | 2/1987 | Smits |
| 4,693,253 | A | 9/1987 | Adams |
| 4,708,145 | A | 11/1987 | Tacker, Jr. et al. |
| 4,763,646 | A | 8/1988 | Lekholm |
| 4,774,952 | A | 10/1988 | Smits |
| 4,775,950 | A | 10/1988 | Terada et al. |
| 4,787,389 | A | 11/1988 | Tarjan |
| 4,788,980 | A | 12/1988 | Mann et al. |
| 4,800,883 | A | 1/1989 | Winstrom |
| 4,821,723 | A | 4/1989 | Baker, Jr. et al. |
| 4,827,932 | A | 5/1989 | Ideker et al. |
| 4,834,100 | A | 5/1989 | Charms |
| 4,944,300 | A | 7/1990 | Saksena |
| 4,984,572 | A | 1/1991 | Cohen |
| 4,996,984 | A | 3/1991 | Sweeney |
| 5,007,422 | A | 4/1991 | Pless et al. |
| 5,085,213 | A | 2/1992 | Cohen |
| 5,111,812 | A | 5/1992 | Swanson et al. |
| 5,154,485 | A | 10/1992 | Fleishman |
| 5,161,528 | A | 11/1992 | Sweeney |
| 5,163,428 | A | 11/1992 | Pless |
| 5,178,140 | A | 1/1993 | Ibrahim |
| 5,265,600 | A | 11/1993 | Adams et al. |
| 5,275,621 | A | 1/1994 | Mehra |
| 5,282,836 | A | 2/1994 | Kreyenhagen et al. |
| 5,350,401 | A | 9/1994 | Levine |
| 5,366,485 | A | 11/1994 | Kroll et al. |
| 5,431,682 | A | 7/1995 | Hedberg |
| 5,441,521 | A | 8/1995 | Hedberg |
| 5,464,429 | A | 11/1995 | Hedberg et al. |
| 5,489,293 | A | 2/1996 | Pless et al. |
| 5,522,853 | A | 6/1996 | Kroll |
| 5,928,271 | A | 7/1999 | Hess et al. |
| 5,978,707 | A | 11/1999 | Krig et al. |
| 6,067,471 | A | 5/2000 | Warren |
| 6,718,206 | B2 | 4/2004 | Casavant |
| 7,738,954 | B1 | 6/2010 | Kroll et al. |
| 8,588,907 | B2 | 11/2013 | Arcot-Krishnamurthy et al. |
| 11,071,866 | B2 | 7/2021 | Casavant et al. |
| 11,458,319 | B2 * | 10/2022 | Casavant ............... A61N 1/365 |
| 11,918,814 | B2 * | 3/2024 | Casavant ............ A61N 1/3704 |
| 2002/0120318 | A1 * | 8/2002 | Kroll .................... A61N 1/3627 |
| | | | 607/149 |
| 2006/0224193 | A1 | 10/2006 | Hess |
| 2007/0055184 | A1 | 3/2007 | Echt et al. |
| 2011/0264158 | A1 | 10/2011 | Dong et al. |
| 2011/0307026 | A1 | 12/2011 | Zhu et al. |
| 2011/0319956 | A1 | 12/2011 | Zhu et al. |
| 2013/0158621 | A1 | 6/2013 | Ding et al. |
| 2014/0107724 | A1 | 4/2014 | Shuros et al. |
| 2014/0172035 | A1 | 6/2014 | Shuros et al. |
| 2016/0213272 | A1 | 7/2016 | Pujar |
| 2017/0120058 | A1 | 5/2017 | Ghosh et al. |
| 2019/0126049 | A1 | 5/2019 | Casavant et al. |
| 2019/0126050 | A1 | 5/2019 | Shuros et al. |
| 2020/0009380 | A1 | 1/2020 | Casavant et al. |
| 2022/0168566 | A1 | 6/2022 | Burr |
| 2023/0001199 | A1 | 1/2023 | Casavant et al. |

FOREIGN PATENT DOCUMENTS

| | | |
|---|---|---|
| EP | 0588124 | 3/1994 |
| EP | 3817805 B1 | 4/2022 |
| WO | WO-9528987 A1 | 11/1995 |
| WO | WO-9528988 A1 | 11/1995 |
| WO | WO-9701373 A1 | 1/1997 |
| WO | WO-2014099595 A2 | 6/2014 |
| WO | WO-2019079454 A1 | 4/2019 |
| WO | WO-2020010001 A1 | 1/2020 |

OTHER PUBLICATIONS

"U.S. Appl. No. 16/459,092, Final Office Action mailed Feb. 1, 2022", 18 pgs.

"U.S. Appl. No. 16/459,092, Non Final Office Action mailed Feb. 18, 2021", 16 pgs.

"U.S. Appl. No. 16/459,092, Non Final Office Action mailed Jul. 27, 2021", 16 pgs.

"U.S. Appl. No. 16/459,092, Notice of Allowance mailed May 31, 2022", 9 pgs.

"U.S. Appl. No. 16/459,092, Response filed Mar. 31, 2022 to Final Office Action mailed Feb. 1, 2022", 10 pgs.

"U.S. Appl. No. 16/459,092, Response filed May 17, 2021 to Non Final Office Action mailed Feb. 18, 2021", 10 pgs.

"U.S. Appl. No. 16/459,092, Response filed Oct. 27, 2021 to Non Final Office Action mailed Jul. 27, 2021", 10 pgs.

"U.S. Appl. No. 17/940,886, Non Final Office Action mailed Mar. 31, 2023", 20 pgs.

"U.S. Appl. No. 17/940,886, Notice of Allowance mailed Oct. 25, 2023", 10 pgs.

"U.S. Appl. No. 17/940,886, Response filed Jun. 28, 2023 to Non Final Office Action mailed Mar. 31, 2023", 12 pgs.

"International Application Serial No. PCT/US2019/040144, International Preliminary Report on Patentability mailed Jan. 21, 2021", 7 pgs.

"International Application Serial No. PCT/US2019/040144, International Search Report mailed Sep. 26, 2019", 5 pgs.

"International Application Serial No. PCT/US2019/040144, Written Opinion mailed Sep. 26, 2019", 5 pgs.

Allessie, M, et al., "Regional Control of Atrial Fibrillation by Rapid Pacing in Conscious Dogs", Circulation, 84(4), (Oct. 1991), 1689-1697.

Ayers, Gregory M., et al., "Ventricular Proarrhythmic Effects of Ventricular Cycle Length and Shock Strength in a Sheep Model of Transvenous Atrial Defibrillation", Circulation, 89 (1), (Jan. 1994), 413-422.

Burri, Haran, et al., "Device Programming for His Bundle Pacing", Circulation: Arrhythmia and ElectrophysiologyVolume 12, Issue 2, Feb. 2019 https://doi.org/10.1161/CIRCEP.118.006816, 11 pgs.

Dhingra, R C, et al., "Significance of the HV interval in 517 patients with chronic bifascicular block", Circulation. 64(6), (1981), 1265-71.

Dillon, S M., "Synchronized Repolarization After Defibrillation Shocks", Circulation, 85(5), (May 1992), 1865-1878.

Frazier, D W., et al., "Stimulus-Induced Critical Point—Mechanism for Electrical Initiation of Reentry in Normal Canine Myocardium", Journal of Clinical Investigation, 83, (Mar. 1989), 1039-1052.

Habel, N., et al., "Atrial Oversensing and Optimizing His Bundle Lead Position", In: Natale A., Wang P., Al-Ahmad A., Estes N. (eds) Cardiac Electrophysiology. Springer, Cham., (2020), 569-571.

Kenknight, B H., et al., "Regional Capture of Fibrillating Ventricular Myocardium", Circulation Research, 77(4), (Oct. 1995), 849-855.

Tang, a S., et al., "Three-Dimensional Potential Gradient Fields Generated by Intracardiac Catheter and Cutaneous Patch Electrodes", Circulation, 85 (5), (May 1992), 1857-1864.

Wharton, J M., et al., "Cardiac Potential and Potential Gradient Fields Generated by Single, Combined, and Sequential Shocks During Ventricular Defibrillation", Circulation, 85 (4), (Apr. 1992), pp. 1510-1523.

* cited by examiner

ADJUSTABLE SENSING IN A HIS-BUNDLE PACEMAKER

CLAIM OF PRIORITY

This application is a continuation of U.S. patent application Ser. No. 17/940,886, filed on Sep. 8, 2022, which is a continuation of U.S. patent application Ser. No. 16/459,092, filed on Jul. 1, 2019, which claims the benefit of priority under 35 U.S.C. § 119(e) of U.S. Provisional Patent Application Ser. No. 62/694,825, filed on Jul. 6, 2018, which are herein incorporated by reference in their entireties.

TECHNICAL FIELD

This document relates generally to medical systems, and more particularly, to systems, devices and methods for pacing of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways known as His-Purkinje system to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium may cause dyssynchronous contraction of the heart, resulting in poor hemodynamic performance, including a diminished blood supply to the heart and the rest of the body. For example, an abnormal delay in the transmission of the action potentials in the His bundle can cause irregular or dyssynchronous contractions of the ventricles, resulting in an abnormal rhythm of the heart.

Artificial cardiac pacing system have been used to rectify cardiac dyssynchrony and to improve hemodynamic performance. The artificial cardiac pacing system can provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore synchronous contraction of both ventricles. However, the potential adverse impact on ventricular function produced by the RV apex pacing may still exist in BiV pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall can be complex and challenging in some patients.

Overview

Hemodynamic response to artificial pacing can depend on many factors, including pacing site selection and pacing configurations. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional right ventricular pacing because the activation sequence can be much slower and propagate slowly from the right to the left ventricle across the interventricular septum, thereby causing ventricular dyssynchrony. This sequence of activation results in an uncoordinated contraction which does not occur during biventricular activation through the natural conduction system of the heart. The cells of the natural conduction system can propagate an activation signal about four times faster than working myocardium.

His-bundle pacing (HBP) is an alternative pacing therapy to conventional ventricular pacing in some patients. HBP may activate the heart's natural His-Purkinje system in some patients, and produce efficient and coordinated cardiac contractions. The potentially long-term harmful hemodynamic effects that may occur from continuous RV apex pacing may also be eliminated or reduced. An electrostimulation device that provides conventional ventricular pacing may be configured to deliver HBP. For example, pacing leads or electrodes used for RV pacing may be reconfigured and positioned at the His-bundle region to deliver HBP pulses. Some His-bundle stimulation devices are also capable of sensing cardiac activities, such as electrical activities at the His-bundle region. The detected His-bundle activity may represent His-bundle depolarization in response to an atrial sensed event (AS) (i.e., during a sinus rhythm) or an atrial paced event (AP), an evoked His-bundle response in response to HBP, or a far-field ventricular activity (e.g., a conducted R wave or a premature ventricular contraction (PVC) sensed at the His-bundle region). The His-bundle stimulation device may operate in a demand mode, and deliver HBP only as needed. For example, HBP may be delivered based on whether a His-bundle activity is detected within a predetermined time period following an atrial activity, such as an AP or AS event.

Some patients receiving HBP therapy may have various degrees of heart block. In patients with intermittent heart block, a HBP system may be operated in a command-mode, where HBP pulses are delivered to restore synchronized ventricular activation only when heart block occurs. If there is no evidence of heart block, HBP may be inhibited. Such demand-mode HBP takes advantage of patient physiological conduction through the His-Purkinje system, and delivers pacing only as needed. The demand-mode HBP not only provides therapeutic benefits to the patient, but also improves device functionality such as conserving power of a HBP system.

A challenge in the command-mode HBP is appropriately recognizing a valid inhibitory event indicative of an absence of heart block, such that HBP pulses may be safely inhibited without causing detriment to the patient. In some instances, the His-bundle activity detected at the His-bundle region may not represent a valid inhibitory event (e.g., a His-bundle depolarization or far-field ventricular depolarization including a conducted R wave or a PVC), but rather a far-field atrial activity. Because the electrodes for sensing His-bundle activity can be in close proximity to atrial myocardium, the His-bundle sensing channel may be interfered by atrial activation in the left or right atrium, also referred to as a far-field P-wave (FFPW). In some cases, the FFPW may be strong enough (e.g., a large signal amplitude) to exceed the sensing threshold of the His-bundle sensing channel, causing cross-channel over-sensing of the FFPW. The over-sensed FFPW may be misrecognized as a valid pacing-inhibitory event, causing the HBP therapy to be inappropriately inhibited. Loss of pacing therapy may potentially lead to critical consequences, particularly in patients with heart block and pacemaker dependent.

For at least these reasons, the present inventors have recognized that there is an unmet need for an artificial pacing system that can more effectively detect and properly recognize the His-bundle activity, and deliver HBP therapy only as needed. Embodiments of the present subject matter provide systems, devices, and methods that improve command-mode HBP by distinguishing pacing-inhibitory events from far-field atrial activity. An exemplary medical system includes an electrostimulator to generate HBP pulses to stimulate a His bundle, and a cardiac event detector that may detect a His-bundle activity following an atrial activity. The cardiac event detector may use a cross-chamber blanking or an adjustable His-bundle sensing threshold to prevent over-sensing of far-field atrial activity and inappropriate inhibition of HBP therapy, the. A control circuit may program a demand-mode therapy to the electrostimulation circuit to deliver the HBP pulses if no His-bundle activity is detected within the time window, and withhold the HBP pulse if the His-bundle activity is detected within the time window.

Example 1 is a system for pacing a heart. The system comprises an electrostimulation circuit configured to generate His-bundle pacing (HBP) pulses to stimulate a His bundle of the heart, a cardiac event detector configured to sense a physiologic signal from a His-bundle region and to detect a His-bundle activity from the sensed physiologic signal during a time period following an atrial activity, and a control circuit configured to control the electrostimulation circuit to deliver the HBP pulses if no His-bundle activity is detected within the time period following the atrial activity, and to withhold the HBP pulses if the His-bundle activity is detected within the time period following the atrial activity.

In Example 2, the subject matter of Example 1 optionally includes the atrial activity that may include an atrial sensed event or an atrial paced event.

In Example 3, the subject matter of any one or more of Examples 1-2 optionally includes the cardiac event detector that may be configured to detect the His-bundle activity following a post-atrial cross-chamber blanking period that begins following the atrial activity.

In Example 4, the subject matter of Example 3 optionally includes the post-atrial cross-chamber blanking period that has a fixed duration.

In Example 5, the subject matter of Example 3 optionally includes the post-atrial cross-chamber blanking period that has a first duration if the atrial activity is an atrial sensed event, and a second duration longer than the first duration if the atrial activity is an atrial paced event.

In Example 6, the subject matter of any one or more of Examples 1-5 optionally includes a His-bundle activity detector configured to recognize the detected His-bundle activity as an inhibitory event or a far-field P-wave (FFPW). The control circuit may be configured to program the electrostimulation circuit to deliver the HBP pulses if the detected His-bundle activity is recognized as a FFPW, and to withhold the HBP pulses if the detected His-bundle activity is recognized as an inhibitory event. The inhibitory event may include a conducted His-bundle response, a far-field conducted R-wave, or a premature ventricular contraction.

In Example 7, the subject matter of Example 6 optionally includes the His-bundle activity detector that may be configured to recognize the detected His-bundle activity as an inhibitory event or a FFPW using a timing the detected His-bundle activity.

In Example 8, the subject matter of Example 7 optionally includes the timing of the detected His-bundle activity that may include an atrial-to-His interval (AHI) between the atrial activity and the detected His-bundle activity. The His-bundle activity detector may be configured to recognize the detected His-bundle activity as a FFPW if the AHI is less than 50 milliseconds, or as an inhibitory event if the AHI exceeds 50 msec.

In Example 9, the subject matter of any one or more of Examples 6-8 optionally includes the His-bundle activity detector that may be configured to recognize the detected His-bundle activity as an inhibitory event or a FFPW using a morphology the detected His-bundle activity.

In Example 10, the subject matter of any one or more of Examples 6-9 optionally includes the cardiac event detector that may be configured to adjust an event sensing threshold based on the detected FFPW to detect the His-bundle activity.

In Example 11, the subject matter of any one or more of Examples 1-10 optionally includes the cardiac event detector that may be configured to switch from a first sensing mode to a second sensing mode to detect the His-bundle activity in response to an indication of HBP, the second sensing mode having a lower sensitivity than the first sensing mode.

In Example 12, the subject matter of Example 11 optionally includes the first sensing mode that may include a first sensing threshold, and the second sensing mode that may include a second sensing threshold higher than the first sensing threshold.

In Example 13, the subject matter of Example 11 optionally includes the first sensing mode that may include a time-varying sensing threshold, and the second sensing mode that may include a time-invariant sensing threshold.

In Example 14, the subject matter of any one or more of Examples 11-13 optionally includes an arrhythmia detector configured to detect a cardiac arrhythmia, wherein the cardiac event detector is configured to switch to the first sensing mode in response to the detected arrhythmia episode.

In Example 15, the subject matter of Example 14 optionally includes the arrhythmia detector that may be configured to detect a termination of the detected arrhythmia episode. The control circuit may be configured to switch to the second sensing mode in response to the indication of HBP and the detected termination of the arrhythmia episode.

Example 16 is a method for operating a pacing system to stimulate a heart. The method comprises steps of: sensing an atrial activity of the heart using a sensing circuit; detecting a presence or absence of a His-bundle activity from a His-bundle region using a cardiac event detector during a time period following the sensed atrial activity; and delivering His-bundle pacing (HBP) pulses, via an electrostimulation circuit, to stimulate the His bundle of the heart if no His-bundle activity is detected within the time period following the atrial activity, or withholding the delivery of the HBP pulses if the His-bundle activity is detected within the time period following the atrial activity.

In Example 17, the subject matter of Example 16 optionally includes detecting the presence or absence of the His-bundle activity during a post-atrial cross-chamber blanking period that begins following the sensed atrial activity.

In Example 18, the subject matter of any one or more of Examples 16-17 optionally includes steps of: recognizing the His-bundle activity detected within the time period as an inhibitory event or a far-field P-wave (FFPW); and delivering the HBP pulses if the detected His-bundle activity is recognized as a FFPW, or withholding the delivery of the HBP pulses if the detected His-bundle activity is recognized as an inhibitory event. The inhibitory event may include a conducted His-bundle response, a far-field conducted R-wave, or a premature ventricular contraction.

In Example 19, the subject matter of Example 18 optionally includes recognizing the detected His-bundle activity as an inhibitory event or a FFPW using a timing or a morphology of the detected His-bundle activity.

In Example 20, the subject matter of any one or more of Examples 16-19 optionally includes steps of: adjusting an event sensing threshold based on the detected FFPW, and detecting a presence or absence of a His-bundle activity using the adjusted event sensing threshold.

In Example 21, the subject matter of any one or more of Examples 16-20 optionally includes switching from a first sensing mode to a second sensing mode to detect the His-bundle activity in response to an indication of HBP, the second sensing mode having a lower sensitivity than the first sensing mode.

In Example 22, the subject matter of Example 21 optionally includes the first sensing mode that may include a first sensing threshold, and the second sensing mode that may include a second sensing threshold higher than the first sensing threshold.

In Example 23, the subject matter of Example 21 optionally includes steps of detecting a cardiac arrhythmia, and switching to the first sensing mode to detect the His-bundle activity in response to the detected cardiac arrhythmia.

The systems, devices, and methods discussed in this document may improve the technology of cardiac pacing in patients with cardiac disease, such as heart failure. HBP may activate natural His-Purkinje system, thereby preserving ventricular synchrony and improving cardiac performance without structural and functional impairment to the heart. As discussed above, a recognized technological challenge in HBP, particularly the demand-mode HBP, is inappropriate inhibition of HBP due to over-sensing of atrial activity. Inappropriate HBP inhibition may be detrimental to pacemaker-dependent patients having heart block. The present document discusses various approaches to avoid or reduce inappropriate HBP inhibition, including an adjustable His-bundle sensitivity or a post-atrial cross-channel blanking to prevent FFPW over-sensing, or an event recognition circuit and method to distinguish a FFPW from a valid inhibitory event. With better HBP inhibition, the systems and methods discussed herein may improve HBP therapy efficacy with little to no additional cost or system complexity. The avoidance of cross-channel over-sensing of atrial activity, and improved recognition of FFPW, may allow for timely HBP therapy to meet patient needs. Additionally, improved recognition of valid pacing-inhibitory events may result in fewer unnecessary medical interventions, such as drugs, procedures, or device therapies, may be scheduled, prescribed, or provided to such patients. As a result, overall system cost savings may be realized.

The adjustable His-bundle sensing threshold and the recognition of FFPW and valid pacing-inhibitory events as discussed in this document may also improve the functionality of a cardiac pacing system or device. The adjustable sensing threshold expands the utility of the pacing device or system. For example, one pacing device may be configured to pace a ventricle, or to pace the His bundle. More efficient device memory usage may be achieved by storing information of clinical significance, such as the sensing thresholds and/or morphology templates for recognizing a valid inhibitory event or a FFPW. While the recognition of FFPW may prevent inappropriate inhibition of HBP therapy, the recognition of pacing-inhibitory events may help avoid unnecessary device therapies, thereby extending battery life and implantable device longevity. Additionally, device size may be reduced to achieve existing performance metrics.

While His-bundle pacing is specifically discussed in this document, this is meant only by way of example and not limitation. It is within the contemplation of the inventors, and within the scope of this document, that the systems, devices, and methods discussed herein may be applied to stimulate other conductive cardiac tissue, such as the right or left bundle branches or fascicles, or the Purkinje fibers.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for pacing cardiac conductive tissue. An embodiment of the system may include an electrostimulator to deliver His-bundle pacing (HBP) pulses to stimulate a His bundle, and a cardiac event detector to detect a His-bundle activity following an atrial activity. The cardiac event detector may use a cross-chamber blanking or an adjustable His-bundle sensing threshold to prevent over-sensing of far-field atrial activity and inappropriate inhibition of HBP therapy. The electrostimulation circuit may deliver command-mode HBP based on the detected presence or absence of the His-bundle activity. In some examples, the system may recognize the detected His-bundle activity as either a FFPW or a valid inhibitory event, and deliver or withhold HBP therapy based on the recognition of the His-bundle activity.

Figure 1:
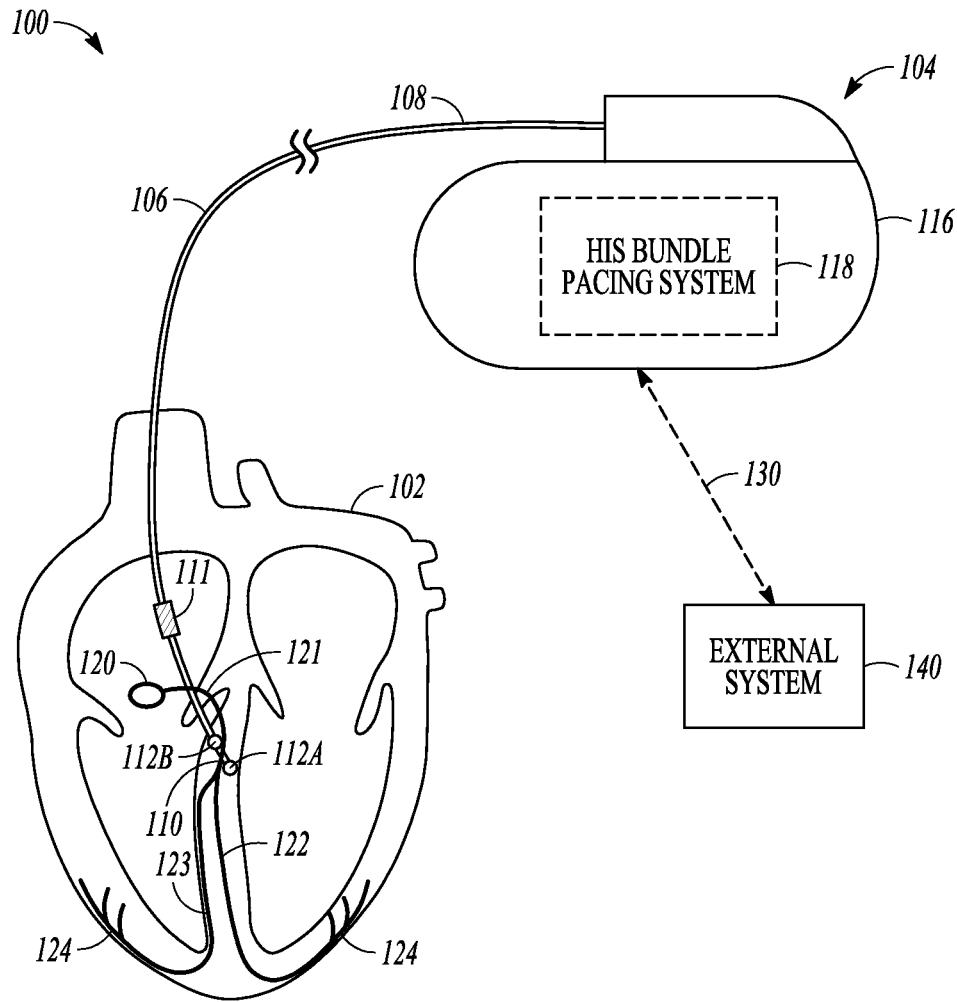
FIG. 1 illustrates generally an example of a cardiac disease management system and portions of an environment in which the system may operate.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patients home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmia or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In various examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or bipolar His-bundle pacing may be selected by a system user from a plurality of candidate electrodes from one or more leads of the lead system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others. In an example, the His-bundle pacing system 118 may sense an atrial activity using one or more electrodes or physiologic sensors. The atrial activity may represent an intrinsic atrial electrical activity such as an atrial sensed event (AS) during a sinus rhythm, or an atrial paced event (AP). In an example, the sensed atrial activity may include an intra-atrial EGM sensed via an electrode positioned within or on the epicardial surface of the left or right atrium, such as an atrial electrode 111 associated with the lead 106 and positioned in the RA. The intra-atrial EGM may alternatively be sensed using an electrode on a dedicated atrial lead, such as an RA lead or an LA lead, as discussed above. In another example, the atrial activity may be detected from a surface ECG. For example, intrinsic atrial activity may be represented by P-waves on an ECG signal, and paced atrial activity may be detected using atrial pacing artifacts on an ECG signal. In various examples, atrial activities may include sensor signals indicative of atrial mechanical contraction. Examples of atrial mechanical signal may include impedance signal, heart sounds signal, or cardiac pressure signals, among others.

The His-bundle pacing system 118 may sense a physiologic signal from the His-bundle region, and detect a His-bundle activity from the sensed physiologic signal. In an example, the physiologic signal may include a His-bundle EGM that may be sensed using one or more of the electrodes 112A and 112B, or other sensing electrodes separated from 112A and 112B. The His-bundle pacing system 118 may detect the His-bundle activity within a specified, such as a predetermined, time period following an atrial activity, such as an AS or an AP event. Detection may be based on a comparison between signal strength of the His-bundle activity and a His-bundle sensing threshold. The detected His-bundle activity may represent His-bundle depolarization in response to the intrinsic or paced atrial depolarization, an evoked His-bundle response in response to HBP at the His-bundle region, or a far-field ventricular activity such as a conducted R wave or a premature ventricular contraction (PVC) sensed at the His-bundle region. In some cases, the detected His-bundle activity may represent far-field atrial activity, such as a FFPW. This may occur when the His-bundle sensing electrodes (e.g., 112A and 112B or other dedicated His-bundle sensing electrodes) are in close proximity to atrial myocardium.

The His-bundle pacing system 118 may deliver demand-mode HBP based on a presence or absence of the His-bundle activity within the time period following an atrial activity. In an example, HBP pulses are delivered, such as via the electrodes 112A and 112B, if no His-bundle activity is detected within the specific time period. HBP pulses are inhibited if a His-bundle activity is detected within the specific time period. To avoid or reduce inappropriate HBP inhibition such as caused by over-sensing of non-inhibitory events such as FFPW, the His-bundle pacing system 118 may adjust the His-bundle sensitivity, or apply a cross-channel blanking period, to detect a His-bundle activity. Alternatively or additionally, the His-bundle pacing system 118 may distinguish a FFPW from a valid inhibitory event, and inhibit HBP therapy only in the presence of a valid inhibitory event but not a FFPW. Examples of His-bundle activity detection and HBP inhibition are discussed below, such as with reference to FIGS. 2-5.

The IMD 104 may be communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may allow a user to control the His-bundle activity detection and recognition, and program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (e.g. HBP delivery or HBP inhibition) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, His-bundle activity detection and recognition information (e.g., His-bundle sensing thresholds and recognition of the His-bundle activity as a valid inhibitory event or a FFPW), among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
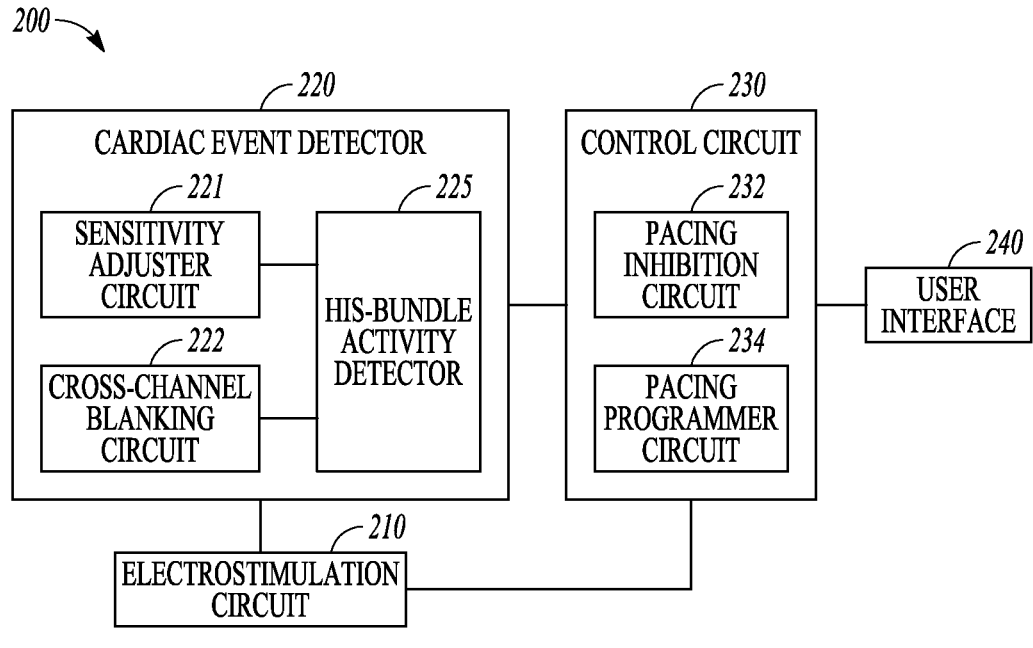
FIG. 2 is a block diagram illustrating an embodiment of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include one or more of an electrostimulation circuit 210, a cardiac event detector 220, a control circuit 230, and a user interface 240.

The electrostimulation circuit 210 may be configured to generate stimulation energy for delivery to the heart 102, such as via one or more leads and the associated electrodes. The electrostimulation circuit 210 may be configured to generate His-bundle pacing (HBP) pulses for delivery to a target pacing site at or near the His bundle such as via the lead 106 and one or more of the electrodes 112A-112B. The target site may include an interventricular septum region or a right atrial region near the His-bundle, or other conductive tissue such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters, such as provided by control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle, among others. Stimulation strength parameters determine the amount of energy delivered to the pacing site, and may include pulse amplitude, pulse width, pulse frequency, pulse waveform, duty cycle, or stimulation duration.

Stimulation mode includes, by way of example and not limitation, an atrial-Hisian (AH) pacing mode, a His-ventricular (HV) pacing mode, or an atrial-His-ventricular (AHV) pacing mode. In the AH pacing mode, the HBP pulses may be delivered only when intrinsic atrial activation (AS), or atrial pacing (AP), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or patients treated with atrioventricular node ablation to slow and regularize ventricular rhythm. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from heart failure with left bundle branch block, heart failure induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an AS or an AP event. An AH timing represents a latency period, within a cardiac cycle, from an intrinsic AS event or an AP event to the delivery of a HBP pulse. In demand HV pacing mode, the ventricular pacing pulses are timed relative to a His pacing event. An HV timing represents a latency period, within a cardiac cycle, from a His bundle event (e.g., a HBP pulse) to the delivery of ventricular pacing pulse. In an example, if the HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an AS or AP event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other unintended cardiac tissue, without direct excitation of the His-bundle fibers, then a para-Hisian pacing results. If no tissue excitation is induced by HBP (e.g., neither the para-Hisian myocardium capture nor the His-bundle capture), then a loss of capture (LOC) results.

The electrostimulation circuit 210 may be capable of generating backup pacing pulses for delivery to the heart to excite the myocardium and prevent asystole. The backup pacing pulses may be delivered when a loss of capture is produced, or alternatively when para-Hisian capture is produced. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes. In an example, the backup pacing may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 milliseconds (msec). With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The cardiac event detector 220 may be coupled to one or more electrodes or physiologic sensors to sense a physiologic signal at the His-bundle region. Examples of the sensed signals may include an electrocardiogram (ECG), an electrogram (EGM) of a portion of the heart such as atrial EGM, ventricular EGM, or evoked His potential, an impedance signal, a heart sound signal, or a pressure signal, among other physiological or hemodynamic signals. The physiologic signal may represent a cardiac response, at the His-bundle region, to intrinsic atrial activation during normal sinus rhythm (AS) or to atrial pacing (AP), or an evoked response to the delivery of HBP. The physiologic signal may also represent far-field ventricular activity such as a conducted R wave or a premature ventricular contraction (PVC) sensed at the His-bundle region, or far-field atrial activity, such as a FFPW.

The sensing circuit 220 may include one or more of a sensitivity adjuster circuit 221 and a cross-channel blanking circuit 222, each of which may prevent or reduce cross-channel over-sensing of FFPW at the His-bundle sensing channel, thus reducing the chances of inappropriately triggering HBP inhibition. The sensitivity adjuster circuit 221 may adjust a sensitivity level, such as an event-sensing threshold. The His-bundle activity detector 225 may detect a His-bundle activity from the sensed physiologic signal using the adjusted sensitivity level. In an example, the sensitivity adjuster circuit 221 may adjust the sensitivity level using a feedback mechanism, such as based on a characteristic of previously detected His-bundle activity by the His-bundle activity detector 225. As to be discussed in the following with reference to FIG. 3, the His-bundle activity detector 225 may recognize the detected His-bundle activity as a valid inhibitory event, or as a FFPW. To prevent over-sensing of FFPW, the sensitivity adjuster circuit 221 may adjust the sensitivity level based on the signal strength (e.g., amplitude) of the valid inhibitory event and/or the signal strength (e.g., amplitude) of the FFPW. In an example, the sensitivity adjuster circuit 221 may raise the event detection threshold to be greater than the amplitude of the FFPW, or a representative FFPW amplitude such as a central tendency of amplitudes of multiple FFPWs. Examples of His-bundle sensing using an adjustable sensitivity to avoid FFPW are discussed below, such as with reference to FIGS. 4A-4B.

In various examples, the sensitivity adjuster circuit 221 may adjust the sensitivity by selecting a sensitivity level from a plurality of predetermined distinct sensitivity levels. Each sensitivity level corresponds to a sensing mode. In an example, the cardiac event detector 220 may selectively operate in a first or a second sensing mode to detect a cardiac event. The first and second sensing modes may have different sensitivity levels, sensing electrode configurations (e.g., sensing vectors), or other sensing parameters. The second sensing mode may have a lower sensitivity, such as a higher detection threshold, than the first sensing mode. Because in some patients the FFPW sensed at the His-bundle sensing channel may have prominent amplitude, the cardiac event detector 220 may use the second sensing mode to sense the His-bundle electrical signal, and use the first sensing mode to sense a ventricular electrical signal. The less sensitive second sensing mode may help prevent over-sensing of FFPW, thereby avoiding inappropriate HBP inhibition. In an example, the second sensing mode corresponds to a detection threshold with a predetermined fixed threshold, such as approximately 10 millivolt in one example. Alternatively, the detection threshold of the second sensing mode may be determined based on previously detected FFPWs, as discussed above. In some examples, the first sensing mode includes a time-varying sensing threshold (e.g., the sensing threshold decays with time), and the second sensing mode includes a time-invariant sensing threshold. The time-invariant sensing threshold may be less sensitive than the time-varying sensing threshold in detecting a cardiac event.

The cardiac event detector 220 may automatically switch between the first and second sensing modes, such as in response to a trigger event. In an example, the cardiac event detector 220 may switch to the second sensing mode (with a higher sensitivity) in response to an indication of HBP. By way of example, the indication of HBP may include an indication of placing a sensing electrode at the His bundle region. In another example, the cardiac event detector 220 may switch to the second sensing mode in response to a delivery of HBP pulses. In yet another example, the switching between the first and second sensing modes may be triggered by a user command.

The cross-channel blanking circuit 222 may apply a blanking period to the His-bundle sensing channel, such that the cardiac event detector 220 will be temporarily suppressed from sensing the physiologic signal (e.g., an EGM) from the His-bundle region during the blanking period. The blanking period is generally designed to avoid inference from certain intrinsic or artificially generated (e.g., paced) signal artifacts. In particular, the cross-channel blanking circuit 222 is instituted to promote appropriate sensing of His-bundle activities that represent a valid inhibitory event (e.g., His-bundle depolarization in response to AS or AP, or a far-field ventricular depolarization or PVC, etc.), and to prevent over-sensing of FFPW.

The cross-channel blanking, hereinafter referred to as post-atrial His-bundle channel blanking (PAHB), may be initiated by an AS or AP event. The cardiac event detector 220 may sense the AS or AP event such as by using electrode 111 on the lead 106, or atrial electrodes associated with an atrial lead. Alternatively, the atrial activation signal may indicate atrial mechanical activity, which may be sensed using a physiologic sensor. The PAHB has a duration sufficiently long to cover the FFPW. The PAHB may have a fixed duration, such approximately 50-70 msec in an example. Alternatively, the PAHB duration may be determined based on patient FFPW timing information gleaned from the patient electrophysiological data, such as time intervals between an AS or AP event sensed at an atrium and a corresponding FFPW sensed at the His-bundle region. In some examples, the PAHB duration may be determined further using timing information of the valid inhibitory events, such as time interval between an AS or AP event and a valid inhibitory event. For example, because the His-bundle sensing electrodes are in closer proximity to right atrium than to left and right ventricles, FFPW may precede far-field ventricular depolarization in time. FFPW may also precede conducted His-bundle depolarization in response to AS or AP in time. The cross-channel blanking circuit 222 may apply a PAHB having a duration that ends in time between FFPW and a valid inhibitory event. Such a PAHB period is advantageous as it offer greater potential of avoiding not only the cross-channel over-sensing of FFPW but also under-sensing of a valid inhibitory event.

As an alternative to fixed PAHB duration, in some examples, a smart blanking may be instituted. The smart blanking combines a PAHB (which may have a shorter duration than the fixed PAHB period) and an automatic adjustment of His-bundle sensitivity, such as a sensing threshold. Distinct PAHB durations may be applied in accordance with the AS or AP event that triggers the blanking. For example, a first PAHB duration may be initiated by an AS event, and a second PAHB duration, longer than the first PAHB duration, may be initiated by an AP event. In an example, the first duration is approximately 15-20 msec, and the second duration is approximately 35-40 msec. The adjustable His-bundle sensing threshold following the PAHB period may reduce the possibility of under-sensing of a valid inhibitory event, such that HBP may be appropriately inhibited when valid inhibitory events are detected. Examples of His-bundle sensing using the PAHB are discussed below, such as with reference to FIG. 4B.

The His-bundle activity detector 225 may detect a His-bundle activity from the sensed physiologic signal. The detection of the His-bundle activity may be within a time period following an AS or AP event, hereinafter referred to an atrio-Hisian (AH) window. The AH window may be programmable. In an example, the AH window may be programmed to approximately 50 msec shorter than a sensed P wave-to-R wave (PR) interval or a programmed atrial-to-ventricular (AV) delay within a cardiac cycle. In another example, the AH window maybe determined based on an intrinsic AH interval, such that the AH window may be programmed to slightly longer than the intrinsic AH interval (e.g., approximately 1-30 msec longer than the intrinsic AH interval). In a demand-mode HBP, HBP pulses may be delivered if no His-bundle activity is detected within the AH window, or inhibited if a His-bundle activity is detected within the AH window.

The His-bundle activity detector 225 is coupled to the sensitivity adjuster circuit 221 and the cross-channel blanking circuit 222. The adjustable His-bundle sensitivity and/or cross-channel blanking may prevent or reduce chances of sensing FFPW within the AH window, such that the detected His-bundle activity is more likely a valid inhibitory event, such as a conducted His-bundle response, a far-field conducted R-wave, or a premature ventricular contraction. In some examples, the His-bundle activity detector 225 may confirm the detected His-bundle activity as either a valid inhibitory event or a FFPW using timing or morphology of the detected His-bundle activity. Examples of His-bundle activity recognition are discussed below with reference to FIG. 3.

In some examples, portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the cardiac event detector 220 and at least a portion of the control circuit 230. The cardiac event detector 220 of the second device may be configured to sense, among other signals, the far-field ventricular response to the HBP pulses. In an example, the first and second devices are both implantable devices. In another example, at least one of the first or the second device is a non-implantable, wearable device.

The control circuit 230 may be coupled to the His-bundle activity detector 225, and configured to control the delivery of HBP pulses based on the presence or absence of a His-bundle activity within the AH window, or additionally based on a recognition of the detected His-bundle activity as provided by the His-bundle activity detector 225. The control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a pacing inhibition circuit 232 and a pacing programmer circuit 234. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The pacing inhibition circuit 232 may generate an inhibition signal to withhold HBP therapy if a His-bundle activity is detected within the AH window, or if the detected His-bundle activity is further recognized as a valid inhibitory event rather than a FFPW. In accordance with the inhibition signal, the electrostimulation circuit 210 withholds the HBP upon the expiration of AH window. If no His-bundle activity is detected within the AH window, or if a His-bundle activity is detected but recognized as a FFPW, then no inhibition signal is generated; and the electrostimulation circuit 210 may deliver the HBP upon the expiration of AH window.

The pacing programmer circuit 234 may include a parameter adjuster circuit to determine or update a stimulation parameter value. The stimulation parameter may be updated manually by a user via a user interface 240. Additionally or alternatively, the stimulation parameter may be updated automatically, such as based on one or more HBP thresholds. The HBP threshold may change over time due to changes in patient pathophysiology, medication, or lead migration or dislodgment. The pacing programmer circuit 234 may include a HBP threshold test circuit to update the HBP threshold, and the parameter adjuster circuit may adjust stimulation strength accordingly to maintain the desired capture status. Shuros et al. U.S. Patent Application No. 62/595,535, entitled "SYSTEMS AND METHODS FOR RECOGNIZING HIS-BUNDLE CAPTURE TYPE AND PROVIDING HIS-BUNDLE PACING," refers to His-pacing capture verification and HBP threshold test, which is incorporated herein by reference in its entirety. The pacing programmer circuit 234 may additionally determine or adjust other parameter such as a stimulation site, or stimulation timing (e.g., AH window) to improve HBP therapy.

The user interface 240 may include an input unit and an output unit. In an example, at least a portion of the user interface 240 may be implemented in the external system 140. The input unit may receive user input such as values of the parameters for physiologic event sensing and user programming of stimulation parameters. The input unit may include an input device such as a keyboard, on-screen keyboard, mouse, trackball, touchpad, touch-screen, or other pointing or navigating devices. The output unit may include circuitry configured to generate a human-perceptible notification of detection of His-bundle activity, recognition of FFPW or valid inhibitory events, and delivery or inhibition of HBP. The output circuit may be coupled to a display for displaying the received physiologic signals, including tracings of one or more of atrial EGM, His-bundle EGM, ventricular EGM, surface electrocardiogram, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about HBP delivery or inhibition. In an example, the output unit may generate an alert when a backup pacing is delivered. In another example, frequent backup pacing delivery may trigger the output unit to generate an alert and prompt a user (e.g., a clinician) to reprogram the pacing system.

Figure 3:
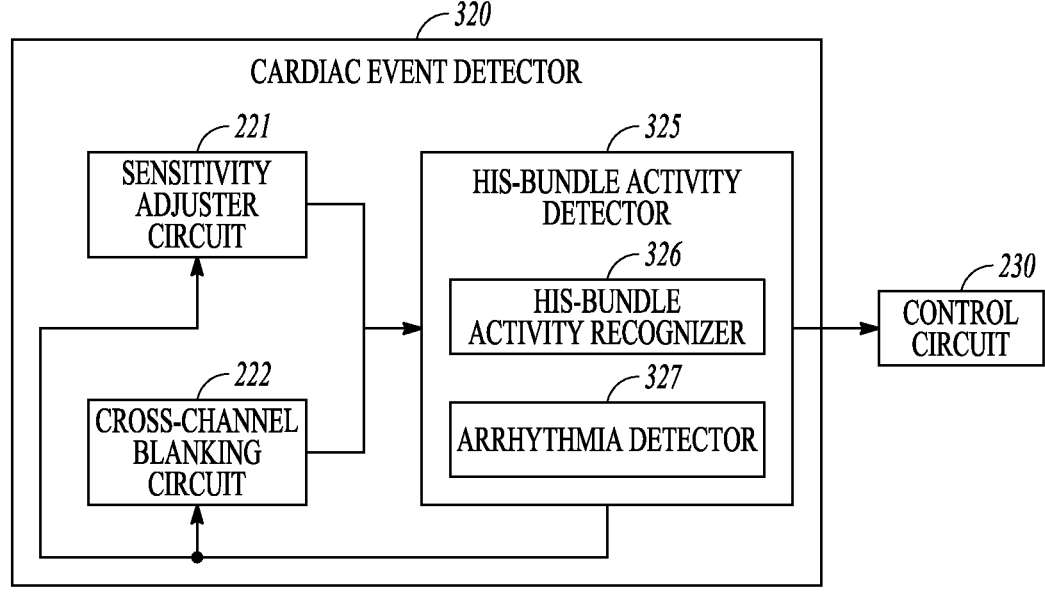
FIG. 3 illustrates generally an example of a cardiac event detector for detecting cardiac events at a His-bundle region.

FIG. 3 illustrates generally an example of a cardiac event detector 320 for detecting cardiac events at a His-bundle region, which can be an embodiment of the cardiac event detector 220 of the His-bundle pacing system 200 as illustrated in FIG. 2. In addition to the sensitivity adjuster circuit 221 and the cross-channel blanking circuit 222 to reduce over-sensing of FFPW as discussed above, the cardiac event detector 320 may include a His-bundle activity detector 325 to further confirm that the detected His-bundle activity is a valid inhibitory event.

The His-bundle activity detector 325 may include a His-bundle activity recognizer circuit 326 configured to recognize a His-bundle activity, which is detected during the AH window, as either a valid inhibitory event or a FFPW. The recognition may be based on timing of the detected His-bundle activity, such as an atrial-to-His interval (AHI) between the atrial activity and the detected His-bundle activity. In an example, the His-bundle activity recognizer circuit 326 compares the AHI to a threshold value, and recognizes the activity as an inhibitory event if the AHI exceeds the threshold, or as a FFPW if the AHI falls below the threshold value. In an example, the AHI threshold is approximately 50 msec. Additionally or alternatively, the His-bundle activity recognizer circuit 326 may recognize the His-bundle activity using a morphology of the detected His-bundle activity. In an example, morphology templates may be created and stored in a storage device for a variety of cardiac events, such as far-field R-wave template, PVC template, conducted His-bundle response template, or FFPW template. Each morphology template may include a set of features extracted or otherwise measured from the respective cardiac event signal morphology. The His-bundle activity recognizer circuit 326 may compare the morphology of the detected His-bundle activity to the morphology templates of one or more cardiac events, and categorize the His-bundle activity based on a similarity metric between the His-bundle activity morphology and the morphology templates. In an example, the His-bundle activity recognizer circuit 326 computes a similarity metric between the His-bundle activity morphology and a FFPW template, and recognizes the detected His-bundle activity as a FFPW if the computed similarity metric falls below a threshold, or as a valid inhibitory event if the computed similarity metric exceeds the threshold. In various examples, the His-bundle activity recognizer circuit 326 may additionally or alternatively perform frequency or spectral analysis, signal transformation such as wavelet transform, or other time-frequency analysis of the detected His-bundle activity, and recognize a FFPW or a valid inhibitory event based on the frequency or spectral components, or features extracted from the transformed signal or time-frequency representation, etc.

The control circuit 230 may control the delivery of HBP based on the recognition of the His-bundle activity. For example, if the His-bundle activity is recognized as a valid inhibitory event, the pacing inhibition circuit 232 may generate an inhibition signal for the electrostimulation circuit to withhold HBP. If the FFPW is recognized, no inhibition signal is generated, and the electrostimulation circuit may delivered HBP upon expiration of the AH window.

The information of the recognized FFPW may be used to update one or more of the His-bundle sensitivity or the cross-channel blanking (e.g., PAHB period). The update of the His-bundle sensitivity or the cross-channel blanking can be initiated if the His-bundle activity recognizer circuit 326 consistently detects and recognizes FFPWs, such as 3-5 consecutive FFPWs or at least 8 FFPW for 10 AS or AP events. As illustrated in FIG. 3, the sensitivity adjuster circuit 221 may adjust the His-bundle sensitivity, such as a His-bundle sensing threshold, based on a signal strength (e.g., amplitude) of the recognized FFPW. In an example, the sensitivity adjuster circuit 221 may increase the His-bundle sensing threshold such as to a level of a central tendency of the amplitudes of the recognized FFPWs plus a specific margin, or switch to a less sensitive sensing mode. Additionally or alternatively, the cross-channel blanking circuit 222 may increase the PAHB period based on the timing of the recognized FFPW. In an example, the cross-channel blanking circuit 222 may increase the PAHB period, such as to a level of a central tendency of the time intervals between the AS or AP event to the FFPWs, plus a specific margin.

The His-bundle activity detector 325 may include an arrhythmia detector circuit 327 that may detect cardiac arrhythmia. Examples of the cardiac arrhythmia include PAC, atrial fibrillation, atrial flutter, PVC, ventricular tachycardia, or ventricular fibrillation, among others. In an example, the control circuit 230 may inhibit HBP in the presence of detected cardiac arrhythmia. In some examples, the detected arrhythmia may be used to adjust His-bundle sensitivity or the cross-channel blanking. For example, in the presence of an atrial or ventricular tachyarrhythmia, the sensitivity adjuster circuit 221 may temporarily increase the sensitivity level, or suspend the less-sensitive second sensing mode and revert to the more-sensitive first sensing mode, to sense the cardiac activity. Switching to a higher sensitivity may help detect arrhythmia, and prevent hemodynamic instability and potentially life-threatening events. Additionally, during an arrhythmic event such as atrial fibrillation or atrial flutter, atrial activity strength (e.g., signal amplitude) may be weak, such that FFPW is less likely to be oversensed in the His-bundle channel. Similarly, in the presence of an atrial or ventricular tachyarrhythmia, the cross-channel blanking circuit 222 may temporarily reduce the PAHB period to facilitate arrhythmia detection at the His-bundle region. The arrhythmia detector circuit 327 may further detect a termination of the detected arrhythmia episode. In response to the arrhythmia termination, the sensitivity adjuster circuit 221 may decrease the sensitivity level, or switch back to the less-sensitive second sensing mode. The cross-channel blanking circuit 222 may similarly extend the PAHB period upon the termination of the arrhythmia termination.

Figure 4A:
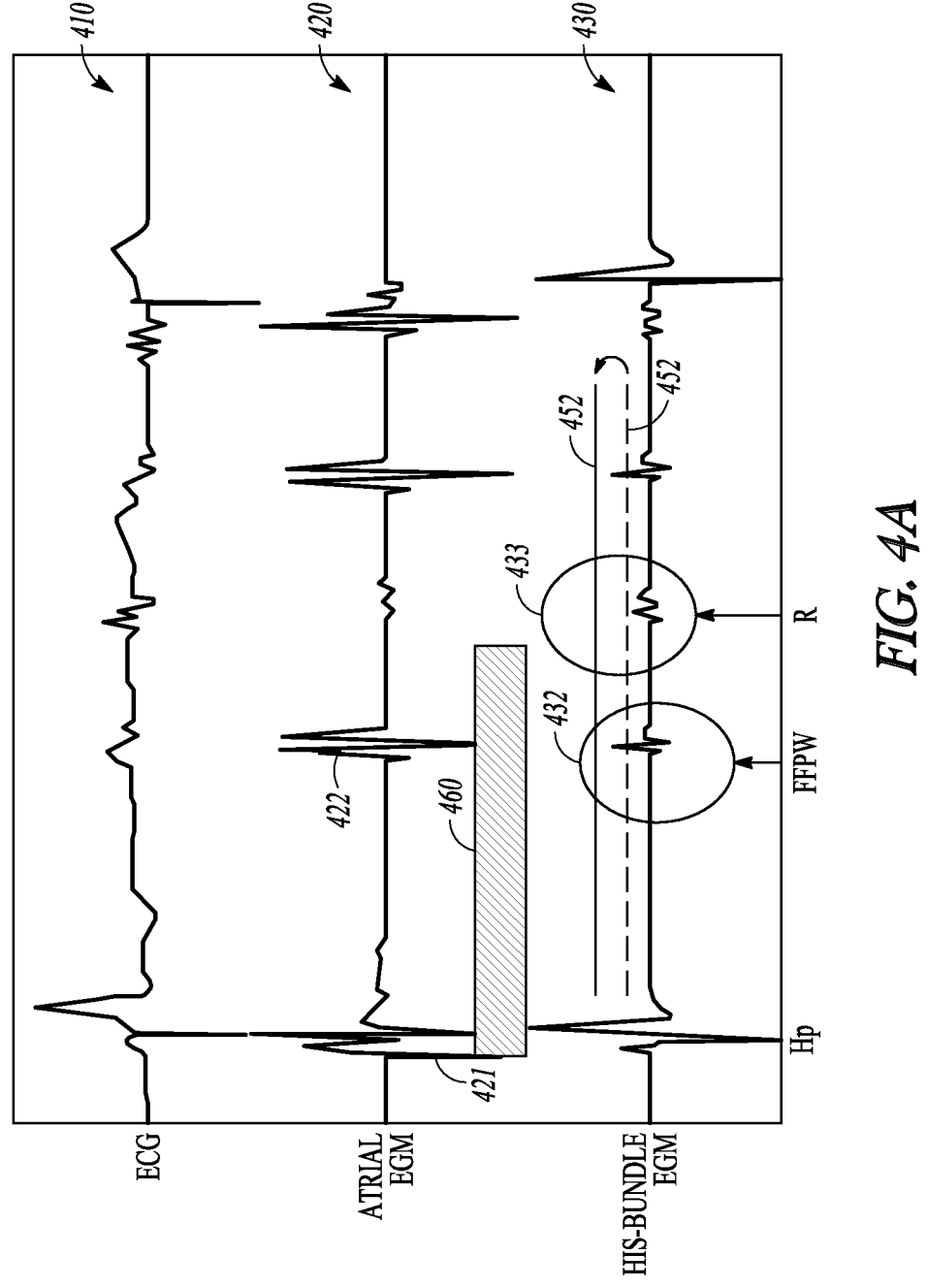
FIGS. 4A-4B illustrates generally examples of His-bundle event sensing to avoid cross-channel over-sensing of FFPW.
Figure 4B:
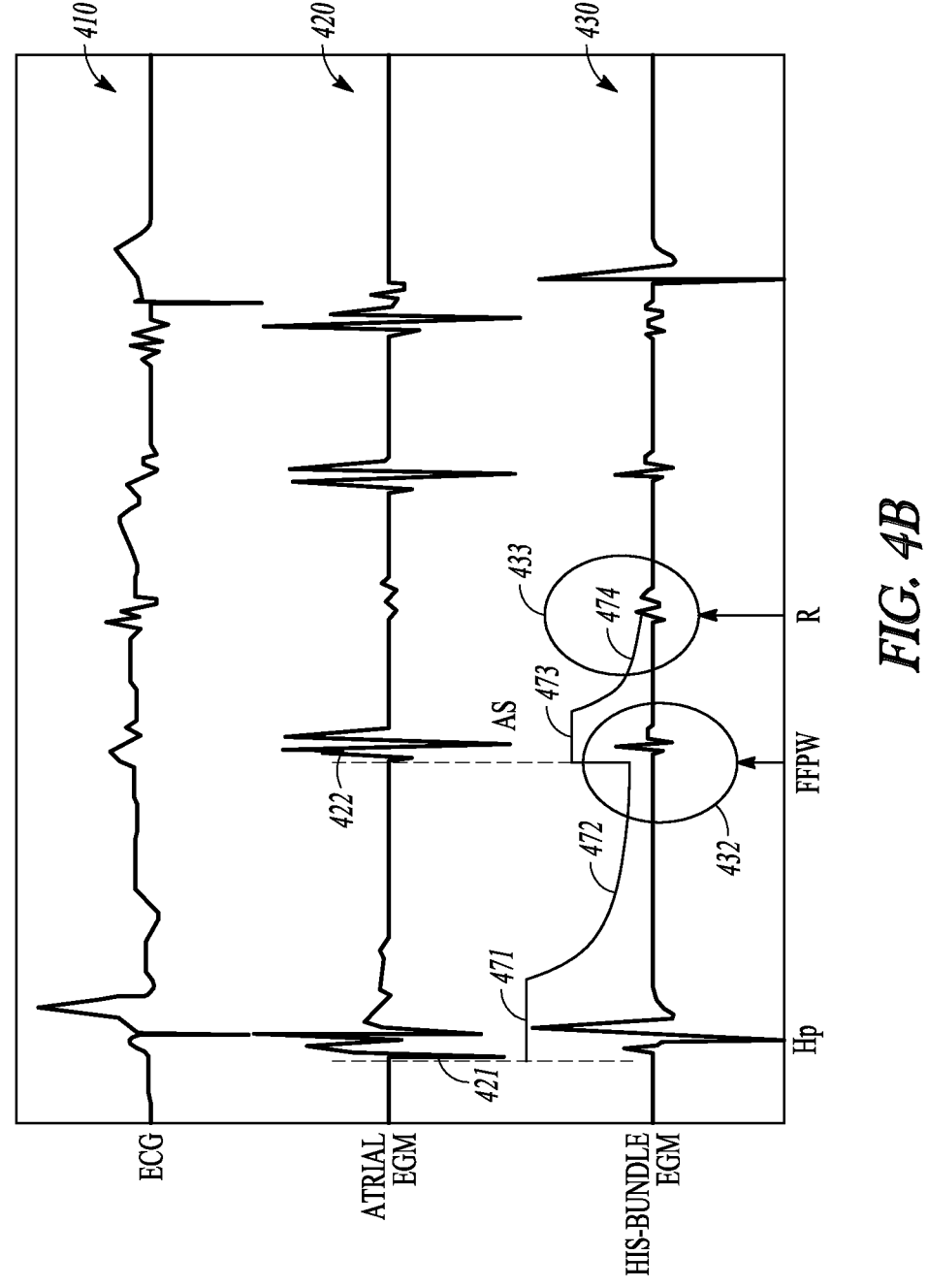

FIGS. 4A-4B illustrates generally examples of adjusting His-bundle sensing threshold to avoid cross-channel oversensing of FFPW. As discussed above, in some patients the FFPW may have a large amplitude comparable to or larger than a valid inhibitory event such as conducted R waves detected from the His-bundle region. The detection of the His-bundle may trigger inappropriate HBP inhibition, which can be detrimental to patient with intermittent heart block. FIG. 4A illustrates an adjustable sensitivity, such as provided by the sensitivity adjuster circuit 221, to avoid or reduce cross-channel over-sensing of FFPW. An ECG signal 410, an atrial EGM 420, and a His-bundle EGM 430 may be concurrently recorded by respective sensing circuits from a patient and recorded. The ECG signal 410 may be sensed using surface electrodes or electrodes associated with an implantable or wearable device. The atrial EGM 420 may be sensed using electrode 111. The His-bundle EGM 430 may be using electrodes 112A-112B.

As shown in the signal segments in FIG. 4A, following an atrial pace (AP) 421, electrical activities are monitored and detected from the His-bundle channel 420 using an adjustable sense threshold. An intrinsic atrial sense (AS) event 422 then occurs. At approximately the same time, FFPW 432 appears on the His-bundle sensing channel, likely due to close proximity of His-bundle sensing electrodes to the atrium. If a low sensing threshold 451 (corresponding to a more sensitive mode) is used to sense the His-bundle activity, the FFPW 432 would exceed the sensing threshold 451 and get detected by the His-bundle activity detector 225 or 325. Such an over-sensing of FFPW 432 in the His-bundle channel inappropriately may inhibit the HBP from being delivered. To prevent FFPW over-sensing, the sensitivity adjuster circuit 221 may use a lower His-bundle sensitivity, such as a sensing threshold 452 higher than the threshold 451. The threshold 452 can be programmed to a level higher than the FFPW amplitude to avoid over-sensing of FFPW and HBP inhibition.

A far-field R wave 433 following the FFPW 432 has a smaller amplitude than the FFPW 432. The far-field R wave 433, which is a valid inhibitory event, falls below the threshold 452; and therefore would be under-sensed. This may be mitigated using the AH window 460 that begins at the AS event 421 and has a predetermined duration of slightly shorter than PR interval. His-bundle sensing is performed at threshold 452 within the AH window 460, and at threshold 451 outside the AH window 460. Because far-field R wave 433 falls outside the AH window 460, it may be detected using the lower threshold 451, such that HBP may be appropriately inhibited in response to a detection of the far-field R wave 433.

FIG. 4B illustrates another approach to avoid or reduce cross-channel over-sensing of FFPW in the His-bundle sensing channel using a post-atrial His-bundle blanking (PAHB) period, such as provided by the cross-channel blanking circuit 222. The same signal segments as illustrated in FIG. 4A are also shown in FIG. 4B. The AP event 421 initiates a PAHB period 471, during which no His-bundle activity is sensed. A sensing threshold 472 is used to detect His-bundle activity immediately after the expiration of the PAHB period 421. The sensing threshold 472 may be adjustable. In an example, the sensing threshold 472 may be a time-varying threshold that decreases over time, as shown in FIG. 4B. Alternatively, the sensing threshold 472 may a fixed threshold. Subsequently, a next AS event 422 initiates another PAHB period 473, during which the event sensing is blocked at the His-bundle channel. The post-AS PAHB period 473 may be identical to the post-AP PAHB period 471. Alternatively, the post-AS PAHB period 473 may be shorter than the post-AP PAHB period. As the FFPW 432 falls within the PAHB period 473, it would not be detected even though it has a large amplitude. HBP inhibition at time of FFPW may therefore be avoided.

Immediately following the expiration of the PAHB period 473, a sensing threshold 474 may be applied to detect His-bundle activity. The sensing threshold 474 may have a fixed sensitivity, or time-varying such as decaying over time at shown in FIG. 4B. The subsequent far-field R wave 433 exceeds the sensing threshold 474, and can be properly detected. HBP is appropriately inhibited at time of the far-field R wave 433.

Figure 5:
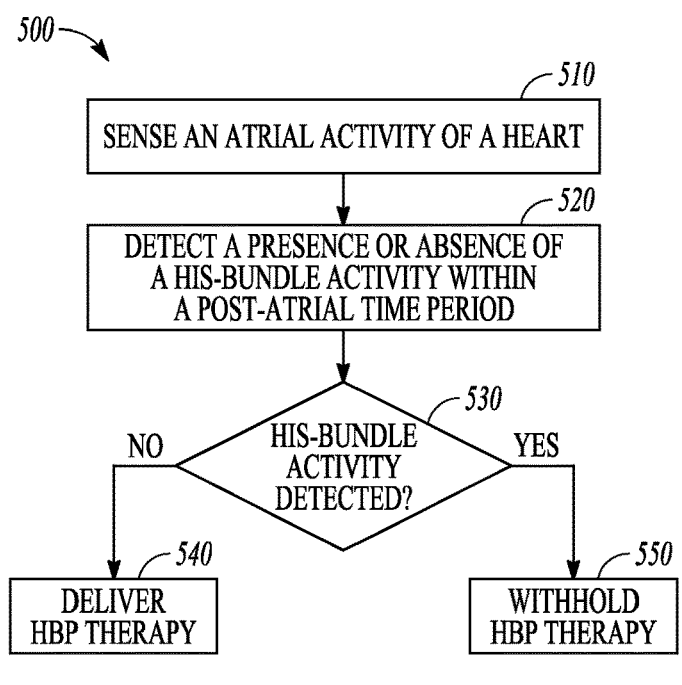
FIG. 5 is a flowchart illustrating generally an example of a method for providing HBP to a patient.

FIG. 5 is a flowchart illustrating generally an example of a method 500 for providing His-bundle pacing to a patient using a medical system. The method 500 may be implemented and executed in an ambulatory medical device, such as an implantable or wearable medical device, or in a remote patient management system. In an example, the method 500 may be implemented in, and executed by, the IMD 104, one or more devices in the external system 140, or the His-bundle pacing system 200.

The method 500 commences at 510, where an atrial activity may be sensed from a patient heart, such as by using the cardiac event detector 220. The atrial activity may represent an intrinsic atrial electrical activity such as an atrial sensed event (AS) during a sinus rhythm, or an atrial paced event (AP). The atrial activity may include atrial electrical activity (e.g., atrial EGM sensed via an electrode positioned within or on the epicardial surface of the left or right atrium, or P-waves on an ECG signal), or atrial mechanical activity such as sensed using an impedance sensor, heart sound sensor, or cardiac pressure sensor, among others.

At 520, a presence or absence of a His-bundle activity may be detected from a His-bundle region, such as by using the His-bundle activity detector 225. A physiologic signal may be sensed from the His-bundle region. In an example, the physiologic signal may include a His-bundle EGM sensed using one or more of the electrodes 112A and 112B. The physiologic signal may represent a cardiac response, at the His-bundle region, to atrial activation such as an AS or an AP event, an evoked response to the HBP pulses delivered at the His-bundle region, far-field ventricular activity, or far-field atrial activity such as a far-field P-wave (FFPW). A FFPW may occur when the His-bundle sensing electrodes are in close proximity to atrial myocardium. In some instances, the FFPW may have a large amplitude in the His-bundle sensing channel. Detection of the FFPW may cause inappropriate inhibition of HBP therapy, which can be detrimental of patients with intermittent heart block.

The His-bundle activity may be detected within a specified time period, or an AH window, following the sensed atrial activity (e.g., an AS or an AP event). The AH window may be programmed to approximately 50 msec shorter than a sensed P wave-to-R wave (PR) interval or a programmed atrial-to-ventricular (AV) delay within a cardiac cycle. In another example, the AH window maybe determined based on an intrinsic AH interval, such that the AH window may be programmed to slightly longer than the intrinsic AH interval (e.g., approximately 1-30 msec longer than the intrinsic AH interval).

His-bundle activity may be detected within the AH window using a comparison of the signal strength of the His-bundle activity and a His-bundle sensing threshold. A His-bundle activity is deemed present if the signal strength exceeds the His-bundle sensing threshold, or is deemed absent if the signal strength falls below the His-bundle sensing threshold. To prevent or reduce over-sensing of FFPW in the His-bundle sense channel and inappropriate inhibition of HBP therapy, an adjustable His-bundle sensitivity or a cross-channel blanking may be used. The adjustable His-bundle sensitivity allows the His-bundle activity to be sensed at different sensing modes each having respective and distinctive sensitivity levels. In an example, if HBP is indicated, a less sensitive sensing mode may be used to help prevent over-sensing of FFPW, such as by using the sensitivity adjuster circuit 221. The less sensitive sensing model may correspond to a detection threshold with a predetermined fixed threshold, such as approximately 10 millivolt in one example. In some examples, the detection threshold corresponding to the less sensitive sensing mode may be determined based on previously detected FFPWs, as to be discussed below with reference to FIG. 6. In some examples, the less sensitive sensing mode may include a time-invariant sensing threshold. Compared to a time-varying sensing threshold (e.g., the sensing threshold decays with time), the time-invariant sensing threshold may be less sensitive, such that over-sensing of FFPW may be avoided or reduced.

Additionally or alternatively, a cross-channel blanking period may be used to temporarily suppress cardiac sensing during the cross-channel blanking period, such as by using the cross-channel blanking circuit 222. A post-atrial His-bundle channel blanking (PAHB) period may be initiated by an AS or AP event. The PAHB period may be programmable. In an example, the PAHB period has a fixed duration, such as approximately 50-70 msec. In another example, the PAHB period may be determined based on patient FFPW timing information, as to be discussed below with reference to FIG. 6. In some examples, distinct PAHB period may be applied in accordance with the AS or AP event that triggers the blanking. For example, a first PAHB period may be initiated by an AS event, and a second PAHB period, longer than the first PAHB duration, may be initiated by an AP event. In some examples, a smart PAHB may be used, including a PAHB followed by an automatically adjustable His-bundle sensing threshold that may reduce the possibility of under-sensing of a valid inhibitory event, such that HBP may be appropriately inhibited when valid inhibitory events are detected.

At 530, if a His-bundle activity is detected within the AH window, then a HBP therapy is withheld at 550. If no His-bundle activity is detected within the AH window, then at 540 a HBP therapy is delivered to a target site, such as upon expiration of the AH window. The target site may include a region at or near the His bundle 121, such as a region distal to the blocked or slowly conducting AV node and in the AV septum, an interventricular septum region, or a right atrial region near the His-bundle 121. The HBP pulse may be generated by the electrostimulation circuit 210, according to programmed stimulation parameters. Examples of the stimulation parameters may include stimulation site, stimulation mode, stimulation timing, or stimulation strength, among other parameters. The stimulation strength parameters determine the amount of energy delivered to the pacing site, and may include pulse amplitude, pulse width, pulse frequency, pulse waveform, duty cycle, or stimulation duration. In an example, the HBP pulses may be programmed with different stimulation strength values, such as pulse amplitudes. In an example, HBP pulses may be delivered in multiple cardiac cycles, such that at least one pulse is delivered within each of the multiple cardiac cycles.

Figure 6:
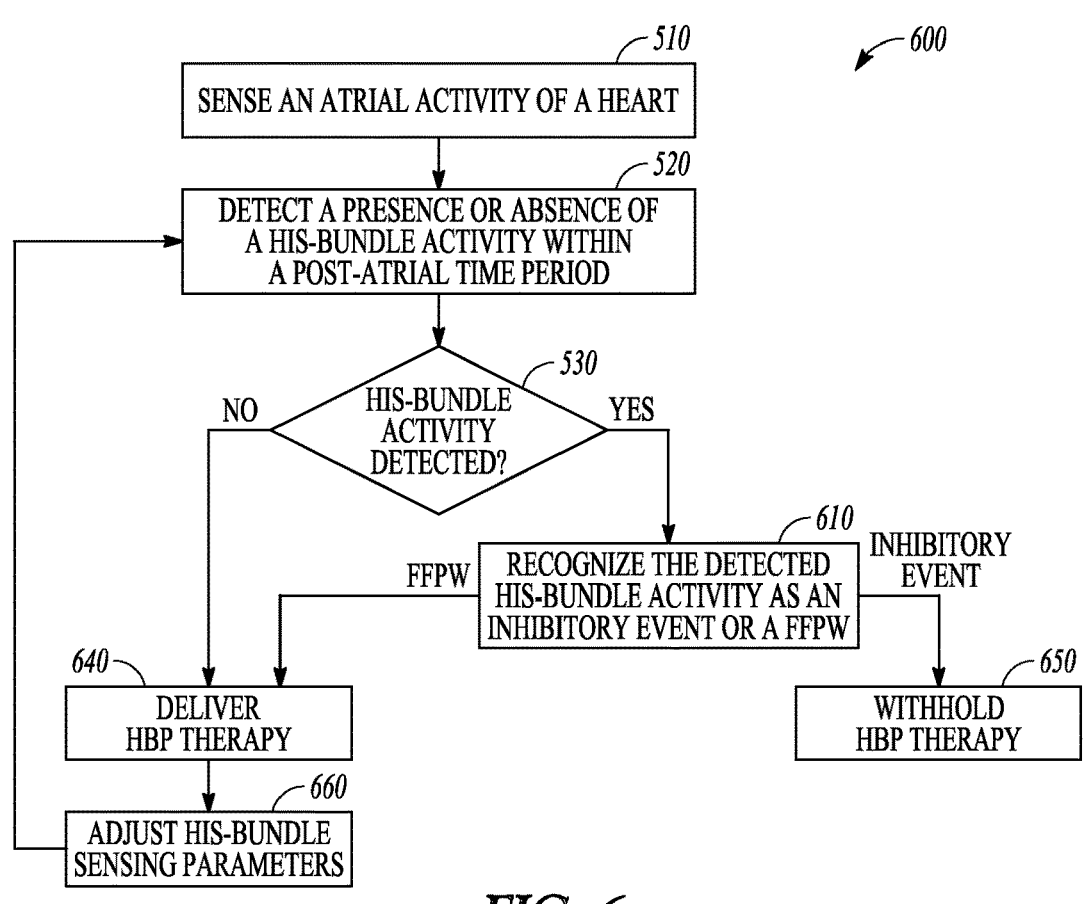
FIG. 6 is a flowchart illustrating generally an example of a method for providing HBP to a patient using FFPW characteristics.

FIG. 6 is a flowchart illustrating generally a method 600 for providing His-bundle pacing to a patient using FFPW characteristics. The method 600 represents a variant of the method 500, and may be implemented in and executed by the IMD 104 or the His-bundle pacing system 200.

The method 600 includes steps of sensing an atrial activity at 510, and detecting a presence or absence of a His-bundle within an AH window at 520, similar to the method 500 as discussed above. If the His-bundle activity is determined to be present at 530, then the detected His-bundle activity may be recognized as either a valid inhibitory event or a FFPW, such as by using the His-bundle activity recognizer circuit 326. The recognition may be based on timing, morphology, or frequency or spectral components of the detected His-bundle activity, as discussed above with reference to FIG. 3. If the sensed His-bundle activity is recognized as a valid inhibitory event, such as a conducted His-bundle response, a far-field conducted R-wave, or a premature ventricular contraction, then HBP therapy may be withheld at 650. If the sensed His-bundle activity is recognized as a FFPW, the HBP therapy may be delivered at 540.

At 660, one or more His-bundle sensing parameters may be adjusted using the recognized FFPW, such as to update one or more of the His-bundle sensitivity or the cross-channel blanking (e.g., PAHB period). In an example, the His-bundle sensitivity, such as a His-bundle sensing threshold, may be adjusted based on a signal strength (e.g., amplitude) of the recognized FFPW. For example, the His-bundle sensing threshold may be increased to a level of approximately a central tendency of the amplitudes of the recognized FFPWs, plus a specific margin. In another example, the PAHB period may be adjusted based on the timing of the recognized FFPW. For example, the PAHB period may be increased to a level of a central tendency of the time intervals between the AS or AP event to the FFPWs, plus a specific margin. Because in some instances the FFPW may precede a valid inhibitory event in time, the PAHB period may be determined such that the blanking period ends after the FFPW but before the valid inhibitory event. Such a PAHB period is advantageous as it may not only avoid or reduce cross-channel over-sensing of FFPW, but may avoid or reduce under-sensing of a valid inhibitory event as well. The adjusted His-bundle sensing parameters may be used to detect subsequent His-bundle activity at 520. In some examples, His-bundle sensitivity or the cross-channel blanking may be adjusted when FFPWs are consistently detected.

In some examples, His-bundle sensing parameters, such as the sensitivity level, may be adjusted using information about whether the patient is in a cardiac arrhythmia, such as detected by the arrhythmia detector circuit 327. In an example, a more sensitive His-bundle sensing mode (e.g., a lower sensing threshold) may be used to sense the His-bundle activity in the presence of an atrial or ventricular tachyarrhythmia. A higher sensitivity may help detect arrhythmias, and prevent hemodynamic instability and potentially life-threatening events. Similarly, in the presence of an atrial or ventricular tachyarrhythmia, a shorter PAHB period may facilitate arrhythmia detection at the His-bundle region. Upon arrhythmia termination, the His-bundle sensing threshold, or the PAHB period, may be increased to their respective pre-arrhythmia levels. In some examples, HBP therapy may be inhibited during the detected cardiac arrhythmia.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for pacing a patient's heart, comprising:
an electrostimulation circuit configured to provide electrostimulation energy to an interventricular septum between left and right ventricles of the patient's heart;
a cardiac event detector configured to:
receive atrial information and conduction system information sensed from the patient's heart;
determine a sensing window following atrial activity in the atrial information, the sensing window shorter than a programmed atrial-to-ventricular delay and longer than a patient-specific intrinsic conduction system delay with respect to the atrial activity; and
determine a presence or an absence of conduction system activity in the conduction system information in the determined sensing window; and
a control circuit configured to generate a control signal to the electrostimulation circuit to deliver electrostimulation energy to the interventricular septum in the absence of the conduction system activity in the sensing window, and to withhold delivery of the electrostimulation energy to the interventricular septum in the presence of the conduction system activity in the sensing window.

2. The system of claim 1, wherein the patient-specific intrinsic conduction system delay with respect to the atrial activity includes an intrinsic atrial to left bunch branch delay or an intrinsic atrial to right bundle branch delay.

3. The system of claim 1, wherein the electrostimulation circuit is configured to deliver the electrostimulation energy to the interventricular septum via one or more electrodes positioned at a septal location to activate at least one of a left bundle branch, a right bundle branch, fascicles, or Purkinje fibers.

4. The system of claim 1, wherein, in response to an indication of electrostimulation energy being delivered to the interventricular septum, the cardiac event detector is configured to switch from a first sensing mode to a second sensing mode with a lower sensitivity than the first sensing mode to determine the presence or the absence of conduction system activity in the determined sensing window.

5. The system of claim 4, wherein the first sensing mode includes a first sensing threshold and the second sensing mode includes a second sensing threshold higher than the first sensing threshold.

6. The system of claim 4, wherein the cardiac event detector is configured to detect a cardiac arrhythmia event, and to switch to the first sensing mode in a presence of the detected cardiac arrhythmia event.

7. The system of claim 1, wherein the cardiac event detector is configured to determine the presence or the absence of the conduction system activity using a comparison of the conduction system information in the determined sensing window to an adjustable threshold.

8. The system of claim 1, wherein the atrial activity includes an atrial sensed event or an atrial paced event.

9. The system of claim 1, wherein the cardiac event detector is configured to determine the presence or the absence of the conduction system activity in the determined sensing window following a post-atrial cross-chamber blanking period.

10. The system of claim 1, wherein, in the presence of the conduction system activity:

the cardiac event detector is configured to determine the conduction system activity as an inhibitory event including at least one of a far-field conducted R-wave or a premature ventricular contraction; and the control circuit is configured to generate the control signal to the electrostimulation circuit to withhold delivery of the electrostimulation energy to the interventricular septum when the conduction system activity being determined as the inhibitory event.

11. The system of claim 10, wherein the cardiac event detector is configured to determine the conduction system activity as the inhibitory event using a timing of the conduction system activity or a morphology of the conduction system activity.

12. The system of claim 10, wherein, in the presence of the conduction system activity:

the cardiac event detector is configured to determine the conduction system activity as a far-field P-wave (FFPW); and the control circuit is configured to generate the control signal to the electrostimulation circuit to deliver the electrostimulation energy to the interventricular septum when the conduction system activity is determined as the FFPW.

13. The system of claim 1, wherein the determined sensing window is further shorter than a sensed P wave-to-R wave interval.

14. A method for operating a pacing system to stimulate a patient's heart, the method comprising:

receiving atrial information and conduction system information sensed from the patient's heart;

determining a sensing window following atrial activity in the atrial information, the sensing window shorter than a programmed atrial-to-ventricular delay and longer than a patient-specific intrinsic conduction system delay with respect to the atrial activity;

determining a presence or an absence of conduction system activity in the conduction system information in the determined sensing window; and delivering electrostimulation energy via an electrostimulation circuit to an interventricular septum in the absence of the conduction system activity in the sensing window, and withholding delivery of the electrostimulation energy to the interventricular septum in the presence of the conduction system activity in the sensing window.

15. The method of claim 14, wherein the patient-specific intrinsic conduction system delay with respect to the atrial activity includes an intrinsic atrial to left bunch branch delay or an intrinsic atrial to right bundle branch delay.

16. The method of claim 14, wherein delivering electrostimulation energy to the interventricular septum includes applying the electrostimulation energy to one or more electrodes positioned at a septal location to activate at least one of a left bundle branch, a right bundle branch, fascicles, or Purkinje fibers.

17. The method of claim 14, comprising, in response to an indication of the electrostimulation energy being delivered to the interventricular septum, switching from a first sensing mode to a second sensing mode with a lower sensitivity than the first sensing mode to determine the presence or the absence of conduction system activity in the determined sensing window.

18. The method of claim 17, wherein the first sensing mode includes a first sensing threshold and the second sensing mode includes a second sensing threshold higher than the first sensing threshold.

19. The method of claim 17, comprising:

detecting a cardiac arrhythmia; and switching to the first sensing mode to determine the presence or the absence of the conduction system activity in a presence of the detected cardiac arrhythmia.

20. The method of claim 14, comprising:

determine the conduction system activity as an inhibitory event or a far-field P-wave (FFPW), the inhibitory event including a far-field conducted R-wave or a premature ventricular contraction; and delivering the electrostimulation energy to the interventricular septum when the conduction system activity is determined as the FFPW, or withholding the delivery of the electrostimulation energy to the interventricular septum when the conduction system activity is determined as the inhibitory event.

* * * * *